(12) United States Patent
Matsuo et al.

(10) Patent No.: US 9,402,758 B2
(45) Date of Patent: Aug. 2, 2016

(54) SUPPORTER

(75) Inventors: Kazuhiko Matsuo, Tokyo (JP); Hitoshi Ojima, Osaka (JP)

(73) Assignee: Kowa Company, LTD. (JP)

( * ) Notice: Subject to any disclaimer, the term of this patent is extended or adjusted under 35 U.S.C. 154(b) by 573 days.

(21) Appl. No.: 13/809,500

(22) PCT Filed: Jul. 22, 2011

(86) PCT No.: PCT/JP2011/066653
§ 371 (c)(1),
(2), (4) Date: Jan. 10, 2013

(87) PCT Pub. No.: WO2012/011550
PCT Pub. Date: Jan. 26, 2012

(65) Prior Publication Data
US 2013/0116609 A1  May 9, 2013

(30) Foreign Application Priority Data

Jul. 23, 2010 (JP) .................. 2010-166029

(51) Int. Cl.
*A61F 5/00* (2006.01)
*A61F 5/03* (2006.01)
(Continued)

(52) U.S. Cl.
CPC .............. *A61F 5/03* (2013.01); *A41D 13/0525* (2013.01); *A41D 13/0531* (2013.01); *A61F 5/028* (2013.01); *A61F 13/148* (2013.01); *D04B 21/20* (2013.01); *D10B 2509/028* (2013.01)

(58) Field of Classification Search
CPC ............ A61F 13/08; A61F 2007/0233; A61F 2013/00123; A61F 2013/00238; A61F 2/7812; A61F 5/028; A61F 13/00059; A61F 2002/5056; A61F 2002/7818; A61F 2002/785; A61F 2013/00246; A61F 2013/0028; A61F 5/0111; A61F 5/03; A61F 13/148; A61F 13/64; A61F 5/0193; A61F 5/3784; A61F 5/026; A61F 7/10; A61F 2007/0228; A61F 2007/0231; A61F 5/003; A61F 5/005; A61F 5/0066; A61F 2002/9528; A61F 2007/0022; A45F 2003/144; A45F 3/14; A01F 15/07; A01F 2015/078; A01F 2015/0795; A01F 2015/186; A41F 1/00; A41F 9/002
USPC ........................................ 602/19; 2/336–338
See application file for complete search history.

(56) References Cited

U.S. PATENT DOCUMENTS 3,920,008 A * 11/1975 Lehman ..................... 128/96.1
4,836,194 A * 6/1989 Sebastian et al. .............. 602/19
(Continued)

FOREIGN PATENT DOCUMENTS

CN       1102317 A     5/1995
JP     176298/1976     8/1978
(Continued)

OTHER PUBLICATIONS

International Search Report of International Application No. PCT/JP2011/066653, dated Oct. 25, 2011.

*Primary Examiner* — Michael Brown
(74) *Attorney, Agent, or Firm* — Duquette Law Group, LLC

(57) ABSTRACT

A supporter includes a small number of members and has a simple fitting method. It can give an intraperitoneal pressure rise effect to a supporter wearer, attain retroflexion suppression, and stabilize the sacroiliac joint. The supporter includes a base material which is formed of a knitted fabric by warp knitting and in which a knitting direction of the knitted fabric is set to be a longitudinal direction. Stretchability in the longitudinal direction is given, while stretchability in a short direction is suppressed. It has a back-supporting section that is a central portion of the base material, projection sections provided by projecting upward both end portions disposed on both sides of the back-supporting section, and curved sections each making the vicinity of the boundary between the back-supporting section and each of the projection sections. Each curved section is curved into a shape of approximate "/ \".

5 Claims, 11 Drawing Sheets

(51) Int. Cl.
*A41D 13/05* (2006.01)
*A61F 5/02* (2006.01)
*A61F 13/14* (2006.01)
*D04B 21/20* (2006.01)

(56) References Cited

U.S. PATENT DOCUMENTS

| | | | |
|---|---|---|---|
| 5,111,806 A * | 5/1992 | Travis | 602/19 |
| 5,388,274 A * | 2/1995 | Glover et al. | 2/338 |
| 5,505,692 A * | 4/1996 | Cho | 602/8 |
| 5,628,721 A * | 5/1997 | Arnold et al. | 602/19 |

FOREIGN PATENT DOCUMENTS

| | | |
|---|---|---|
| JP | 1203/1979 | 7/1980 |
| JP | 6-78943 A | 3/1994 |
| JP | 8-191850 A | 7/1996 |
| JP | 9-192152 A | 7/1997 |
| JP | 2002-512547 A | 4/2002 |
| JP | 2002-537947 A | 11/2002 |
| JP | 2003-105615 A | 4/2003 |
| JP | 2003-299683 A | 10/2003 |

\* cited by examiner

Fig. 2(a)
Fig. 2(b)
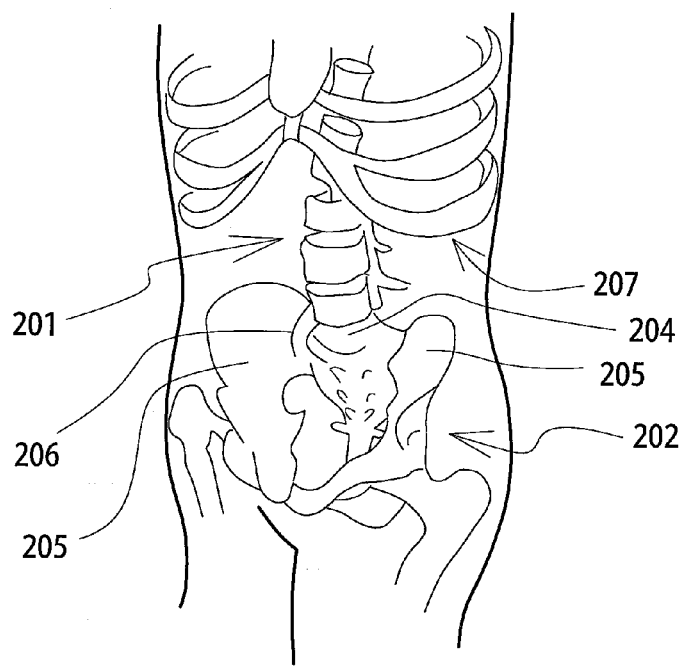
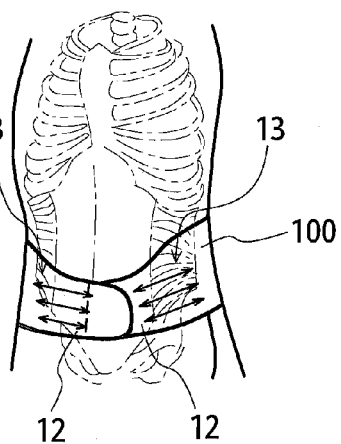
Fig. 2(c)
Fig. 2(d)
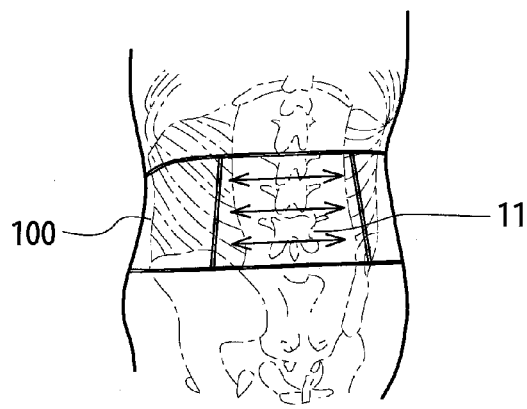
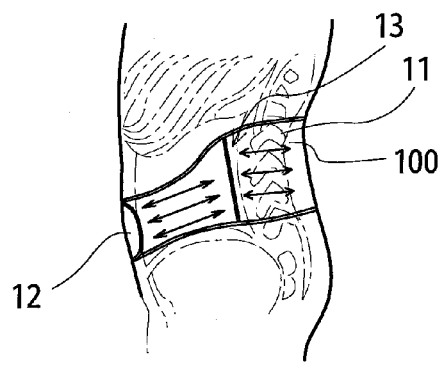

(Forward flexion)　　(Lateral flexion)　　(Retroflexion)

(Lateral flexion)

(Lateral flexion)

Fig. 9 (a)
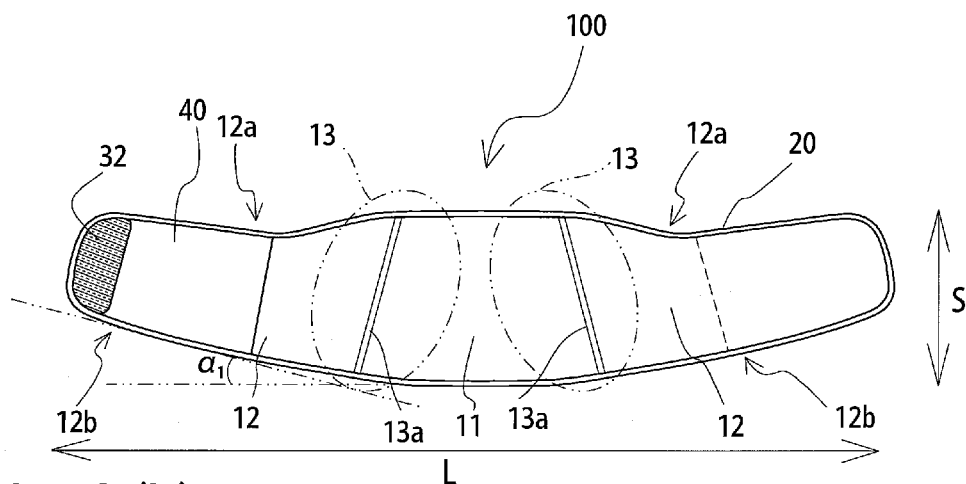
Fig. 9 (b)
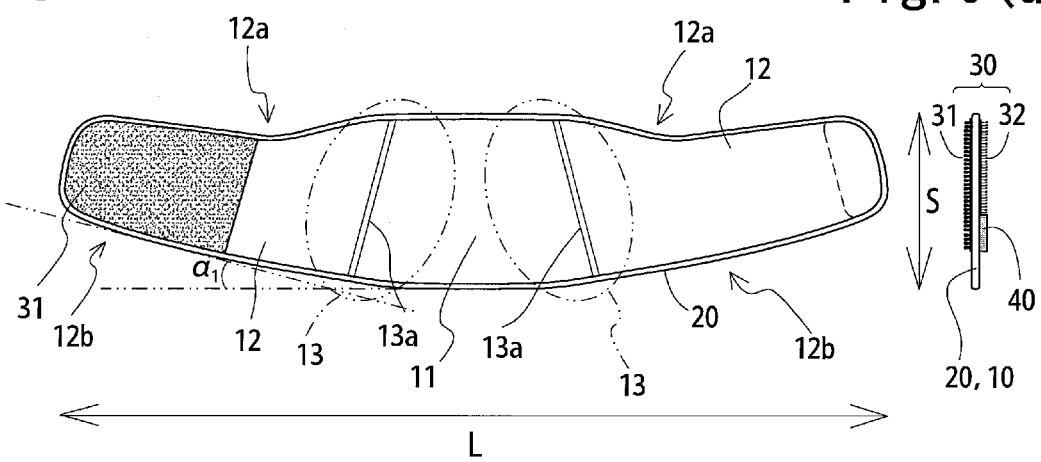
Fig. 9 (d)
Fig. 9 (c)
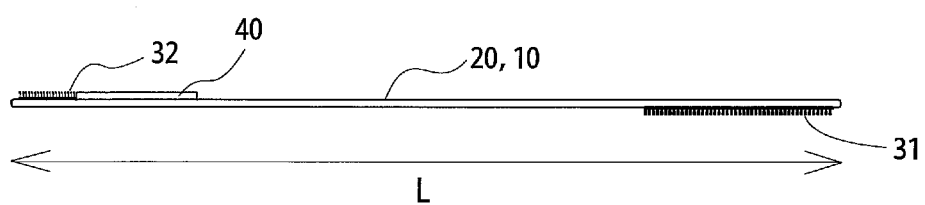

SUPPORTER

TECHNICAL FIELD

The present invention relates to a supporter capable of supporting a wearer's daily motion, and particularly, to a supporter capable of giving a supporter wearer the intraperitoneal pressure rise effect of enhancing pressure in the abdominal cavity so as to support the lumbar vertebrae, attaining retroflexion suppression to suppress the retroflexion movement of the lumbar region, and stabilizing the sacroiliac joint.

BACKGROUND ART

A band-shaped clothing in the related art uses a sweat absorbing and diffusing knitted fabric at least on an inner face and uses a sweat absorbing and diffusing knitted fabric having a diffusion area ratio of 3 or more, or a sweat absorbing and diffusing knitted fabric composed of at least two layers, a hydrophobic back layer and a hydrophilic surface layer (refer to PTL 1, for example).

CITATION LIST

Patent Literature

[PTL 1] JP-A-2003-105615

SUMMARY OF INVENTION

Technical Problem

The band-shaped clothing in the related art is provided with a lining cloth composed of a sweat absorbing and diffusing knitted fabric, an auxiliary belt, and a plastic stay, in addition to a main body belt (a hook-and-loop fastener and an edging member) composed of a mesh-like fabric, and has problems in that the number of members is large and in addition, it is necessary to wrap and fasten the main body belt around the lumbar region by the hook-and-loop fastener and thereafter, tighten the auxiliary belt and then perform fastening by the hook-and-loop fastener, and thus a fitting method is complicated.

The present invention has been made to solve the problem as described above and has an object of providing a supporter in which the number of members is small and a fitting method is simple and which can give an intraperitoneal pressure rise effect to a supporter wearer, attain retroflexion suppression, and stabilize the sacroiliac joint compared to a band-shaped clothing in the related art.

Solution to Problem

A supporter according to the invention includes a base material which is formed of a knitted fabric by warp knitting and in which a knitting direction of the knitted fabric is set to be a longitudinal direction, and stretchability in the longitudinal direction is given, while stretchability in a short direction is suppressed, a back-supporting section that is a central portion of the base material, projection sections provided by projecting upward both end portions composed of both sides of the back-supporting section, and curved sections each making the vicinity of the boundary between the back-supporting section and each of the projection sections be curved into a shape of approximate "/ \".

Advantageous Effects of Invention

In the supporter according to the invention, the supporter includes a base material which is formed of a knitted fabric by warp knitting and in which a knitting direction of the knitted fabric is set to be a longitudinal direction, and stretchability in the longitudinal direction is given, while stretchability in a short direction is suppressed, a back-supporting section which is a central portion of the base material, projection sections provided by projecting upward both end portions composed of both sides of the back-supporting section, and curved sections each making the vicinity of the boundary between the back-supporting section and each of the projection sections be curved into a shape of approximate "/ \", whereby it is possible to give an intraperitoneal pressure rise effect to a supporter wearer, attain retroflexion suppression, and stabilize the sacroiliac joint.

BRIEF DESCRIPTION OF DRAWINGS

FIG. 2(a) is a skeleton diagram for explaining the name of a skeleton in the vicinity of the lumbar region, FIG. 2(b) is a perspective view as viewed from the front right side, showing a wearing state of the supporter shown in FIG. 1, FIG. 2(c) is a perspective view as viewed from the rear right side, showing a wearing state of the supporter shown in FIG. 1, and FIG. 2(d) is a right side view showing a wearing state of the supporter shown in FIG. 1.

FIG. 9(a) is a diagram showing the back fabric face of a supporter related to a second embodiment, FIG. 9(b) is a diagram showing the front fabric face of the supporter shown in FIG. 9(a), FIG. 9(c) is a lower side view of the supporter shown in FIG. 9(a), and FIG. 9(d) is a left side view of the supporter shown in FIG. 9(a).

DESCRIPTION OF EMBODIMENTS

First Embodiment of the Invention

Figure 1A:
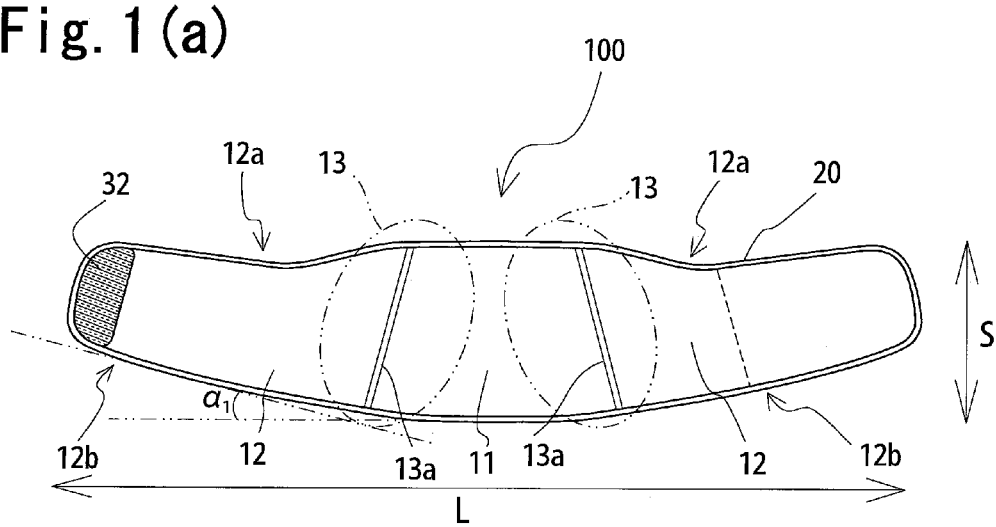
FIG. 1(a) is a diagram showing the back fabric face of a supporter related to a first embodiment.
Figure 1B:
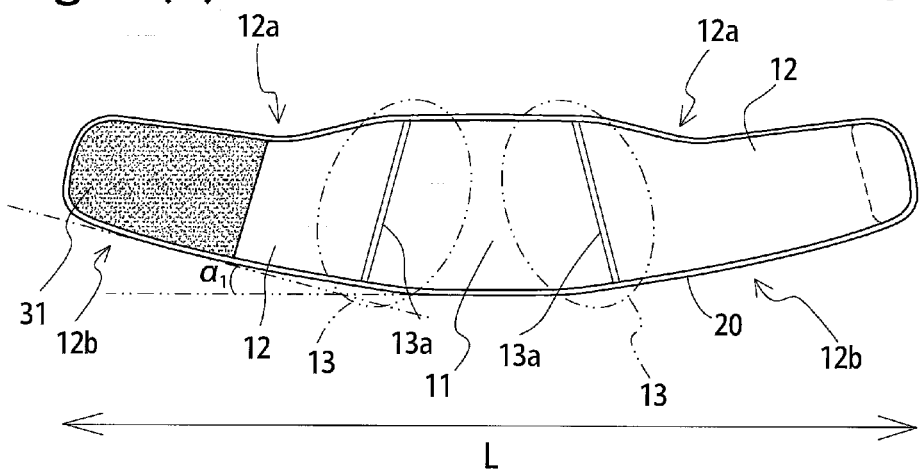
FIG. 1(b) is a diagram showing the front fabric face of the supporter shown in FIG. 1(a)
Figure 1D:
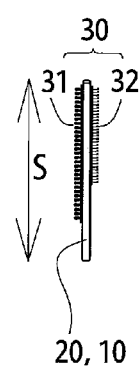
FIG. 1(d) is a left side view of the supporter shown in FIG. 1(a).
Figure 1C:
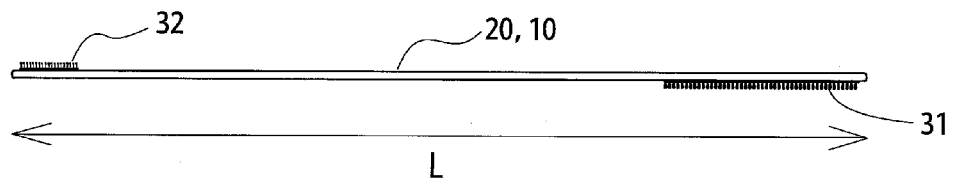
FIG. 1(c) is a lower side view of the supporter shown in FIG. 1(a)

In FIG. 1, a supporter 100 is intended to be used as a supporter for the waist and includes a base material 10 which is formed of a knitted fabric knitted in warp knitting with appearance of one weft yarn by a warp knitting machine (hereinafter referred to as a warp knitted fabric) and in which a knitting direction of the warp knitted fabric is set to be a longitudinal direction L of the supporter 100, and stretchability in the longitudinal direction L is given, while stretchability in a short direction S of the supporter 100 is suppressed.

In addition, the warp knitting machine is classified roughly into a raschel warp knitting machine which forms a knit (a raschel knit) specialized in a pattern by variedly using a needle, and a tricot warp knitting machine which forms a knit (a tricot knit) specialized for high production without assuming a pattern. Further, the raschel warp knitting machine is subdivided into a double raschel warp knitting machine, a Raschelina warp knitting machine, a lace warp knitting machine, a crochet warp knitting machine (a crochet needle knitting machine), and the like.

In the supporter 100 related to this embodiment, the base material 10 is made by cutting a single sheet of warp knitted fabric into a shape shown in FIG. 1 and an edge (a cut face) of the base material 10 is inserted and sewn (bound) in a binder tape 20. However, fray prevention or decoration at the cut face of the base material 10 may also be carried out by edge stitching, bias hemming, or the like. In particular, the binder of the cut face of the base material 10 is preferable because adjacent stitches do not become dense by sewing the binder tape 20 by zigzag stitch and therefore, stretchability in the longitudinal direction L of the base material 10 is not suppressed.

The base material 10 includes a back-supporting section 11 that is a central portion of the base material 10, projection sections 12 provided by projecting upward both end portions disposed on both sides of the back-supporting section 11, and curved sections 13 each making the vicinity of the boundary between the back-supporting section 11 and each of the projection sections 12 be curved into a shape of approximate "/ \".

In the projection sections 12, each of upper sides 12a of both the end portions of the base material 10 is formed by a curved concave portion and each of lower sides 12b of both the end portions of the base material 10 is formed along the extending direction of the upper side 12a.

Further, the projection sections 12 are provided with fastening sections which are disposed on different surfaces of both the end portions of the base material 10 and fasten the different surfaces to each other. In addition, in this embodiment, the supporter 100 using a hook-and-loop fastener 30 as the fastening sections is described. However, as long as it is possible to fasten both the end portions of the base material 10 to each other, it is not limited to a hook-and-loop fastener, and for example, a button, a dot button, a snap, a hook, a buckle, a fastener (a slide fastener or a zip fastener), a front hook, a spindle stop, or the like may also be used.

Further, in the projection sections 12 related to this embodiment, as shown in FIG. 1, a hook 32 of the hook-and-loop fastener 30 is disposed on one end side of a back fabric face which comes into contact with a wearer and a loop 31 of the hook-and-loop fastener 30 is disposed on the other end side of a front fabric face which does not come into contact with the wearer. However, a configuration is also acceptable in which the hook 32 is disposed on the front fabric face and the loop 31 is disposed on the back fabric face, and a configuration is also acceptable in which the side on which the hook 32 is disposed, of the back fabric face, is disposed changed from one end side to the other end side and the side on which the loop 31 is disposed, of the front fabric face, is disposed changed from the other end side to one end side.

The curved sections 13 have approximately "/ \"-shaped reference lines 13a making both end portions of the base material 10 be fastened to each other with the lower sides 12b being continuous, as shown in FIG. 2(b), in a case where fastening is performed by the hook-and-loop fastener 30 (the loop 31 and the hook 32) that is the fastening portion. In this manner, by making both the end portions of the base material 10 be fastened to each other with the lower sides 12b being continuous, a contact area between the loop 31 and the hook 32 is extended, thereby increasing a fastening force, and also the stretching and contracting direction of the base material 10 in the projection section 12 and the curved section 13 is directed upward over the lateral abdomen from the preabdomen, thereby pushing the abdomen up from below, and thus pressure in an abdominal cavity 203 can be increased.

Figure 5A:
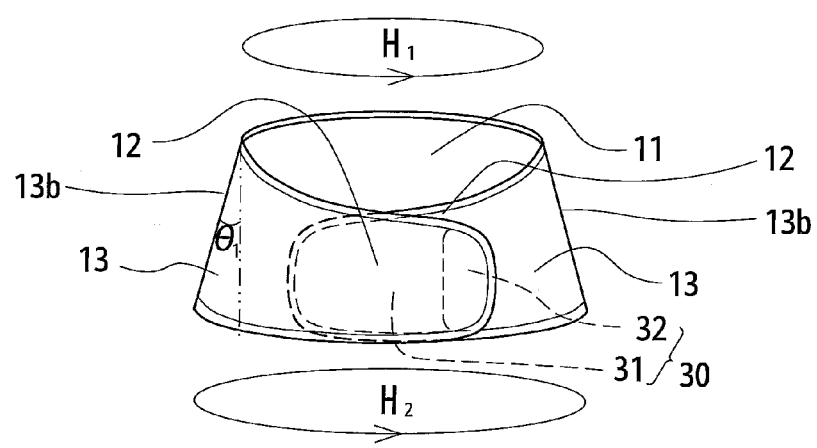
FIG. 5(a) is a front view showing a schematic configuration of the supporter in a case where the supporter has been fastened by fastening sections shown in FIG. 1(a)
Figure 5B:
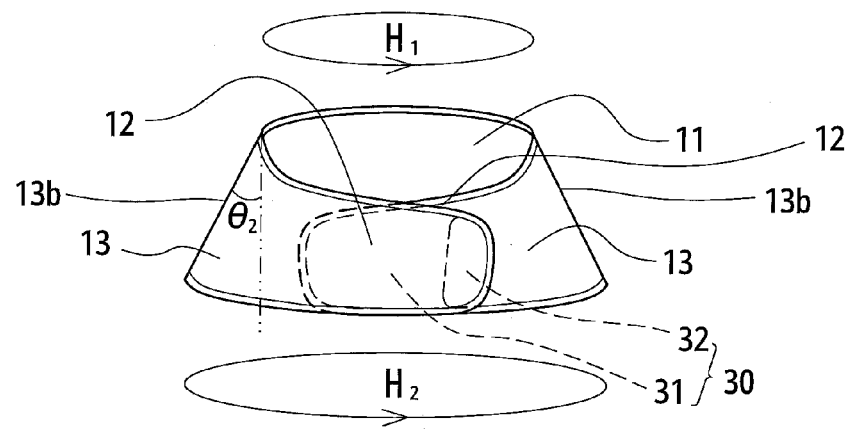
FIG. 5(b) is a front view showing a schematic configuration of the supporter in a case where the supporter has been fastened by fastening sections shown in FIG. 4(a).

In addition, the reference line 13a related to this embodiment is sewn by a decorative stitch. However, if a mark can be provided, it is not limited to a seam (stitch). Further, if the projection sections 12 are bent with the approximately "/ \"-shaped reference lines 13a as references so as to be curved to the lower side (that is, the lower abdomen side of a wearer) and fastened to each other by the hook-and-loop fastener 30 (the loop 31 and the hook 32) that is the fastening portion, after wear on the wearer, as shown in FIG. 5, in a front view, the curved sections 13 form a shape of approximate "/ \" by left and right side end portions 13b.

Here, warp knitting makes a knitted fabric by making loops in a longitudinal direction (a knitting direction) and combining the respective loops by using a large number of warp yarns (warping yarns) arranged in parallel one by one.

As a combining method, there are various types. However, as a typical example, a method of making a knitted fabric as a whole while entangling adjacent warp yarns with each other, or a method of forming a knitted fabric as a whole by making a lot of independent chain stitches with each warp yarn, inserting another set of warp yarns separately prepared into the chain stitches, thereby connecting the chain stitches in a short direction while collecting the chain stitches with several chain stitches can be given.

Further, warp knitting has features such as it being difficult to fray, elongation in a short direction (a direction perpendicular to the knitting direction) being small, high productivity, and a knitting width being large.

A warp knitted fabric is used in the base material 10, whereby desired stretchability is provided to the supporter 100, it is possible to make the thickness of the supporter 100 thin, and even if the fabric is cut, a knitted yarn does not fray from a cut face, and it is possible to process the knitted fabric into a free shape. Further, a warp knitted fabric is used in the base material 10, whereby it is possible to enhance the heat-retention effect of the supporter 100 by a layer of air present in the gap between adjacent knitting yarns.

Further, since the base material 10 is cut from a single sheet of warp knitted fabric, there is no seam due to a plurality of fabrics, shape loss or bending does not easily occur, and in addition, due to a warp knitted fabric having excellent contractibility, the base material 10 can flexibly correspond to the movement of the waist of a wearer (bending, warping, and twisting of the body due to the movement of the pelvis and the backbone) along the concavity and convexity of the body of the wearer.

In addition, in a case where the base material 10 is made by connecting and sewing a plurality of strip-shaped woven fabrics rather than a warp knitted fabric, since the woven fabric has a woven structure which is constituted by warp yarns and weft yarns crossing at right angles up and down according to a certain rule, there is no stretchability in a longitudinal direction and a short direction and it is difficult to fit (suit) the body of a wearer.

Further, in a case where the base material 10 is made by connecting and sewing a plurality of warp knitted fabrics, there is no tension in the base material 10 as a whole, there is no uniformity in elongation, and in addition, bending easily occurs at a seam between adjacent warp knitted fabrics, and a seam spreads, whereby there is a concern that a hole through the fabric may be formed. Further, in a case of forming the base material 10 by connecting and sewing a plurality of warp knitted fabrics, the warp knitted fabrics are superposed on a sewn portion of a seam between adjacent warp knitted fabrics, whereby the supporter 100 is thickened, an increase in the weight of the supporter 100 is caused, and there is a concern that a feeling of wearing of the supporter 100 may be impaired. For this reason, it is preferable that the base material 10 be made cut from a single sheet of warp knitted fabric.

In addition, in the base material 10 related to this embodiment, as a warp yarn knitting the warp knitted fabric, a "Dralon-cotton blend" is used which is a blended yarn of a dry-type acrylic fiber "dralon" (registered trademark) of Dralon GmbH that is soft and has excellent sweat-absorption and quick-drying properties and cotton. In the Dralon-cotton blend, the dry-type acrylic fiber has a structure in which clearance by a beans cross-section is easily formed, and thus a heat-retention effect such as quilting storing air warmed by the body temperature of a wearer can be obtained, and the cotton material that is a natural fiber having excellent moisture absorption properties is gentle on the skin of a wearer, is flexible, and absorbs sweat, thereby being able to make the touch of the supporter 100 (the base material 10) better.

Next, the operation and effects of the supporter 100 will be described using FIGS. 2 and 3. In addition, in FIGS. 2(b) to 2(d), the stretching and contracting direction of the base material 10 of the supporter 100 is shown by an arrow.

Here, the waist is constituted by lumbar vertebrae 201 in which five bones are stacked and a pelvis 202, as shown in FIG. 2(a). Further, the lumbar vertebrae 201 is supported by a group of abdominal muscles such as the lateral abdominal muscles and the posterior abdominal muscles, which are present in the abdomen, or a group of back muscles such as the superficial back muscles and the deep back muscles, which are present in the back.

Figure 3A:
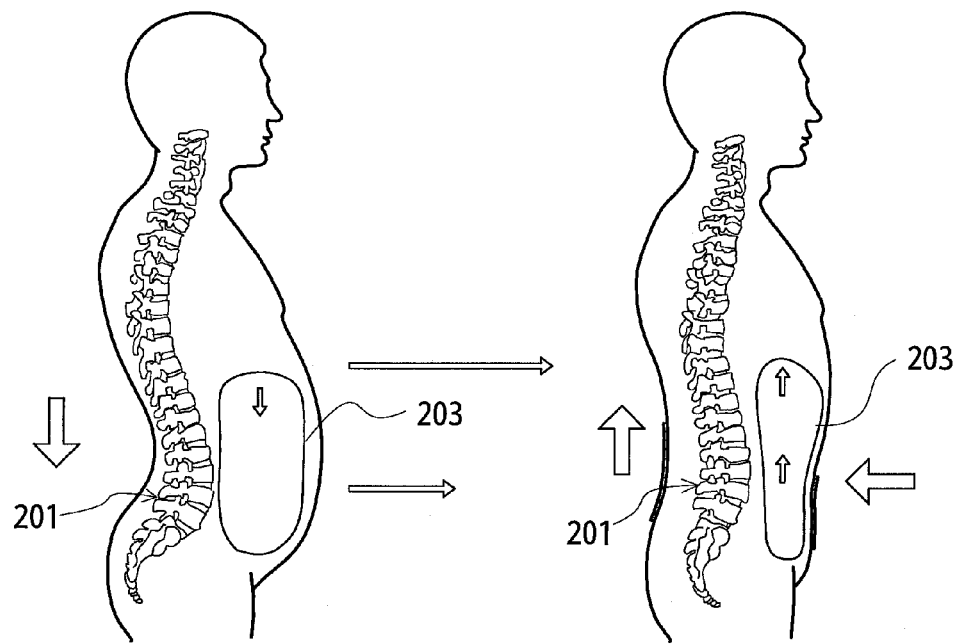
FIG. 3(a) is an explanatory diagram for explaining an intraperitoneal pressure rise effect.

For this reason, in order to alleviate lumbago, it is effective to support the lumbar vertebrae 201 by holding the circumference of the waist from the outside and pushing the abdomen up from below, as shown in FIG. 3(a), thereby increasing pressure in the abdominal cavity 203 (an intraperitoneal pressure rise effect).

Figure 3B:
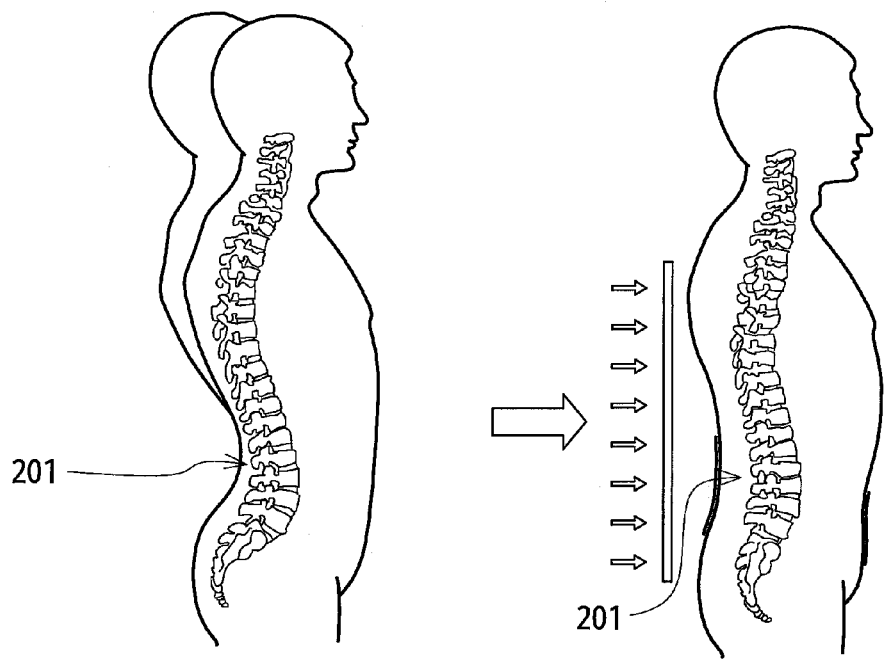
FIG. 3(b) is an explanatory diagram for explaining retroflexion suppression.
Figure 4A:
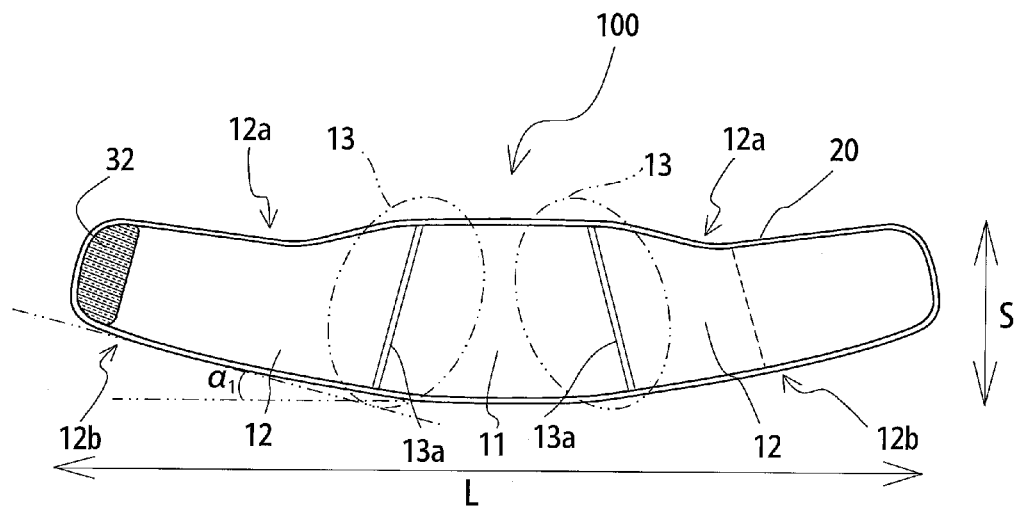
FIG. 4(a) is a diagram showing the back fabric face of another supporter related to the first embodiment.
Figure 4B:
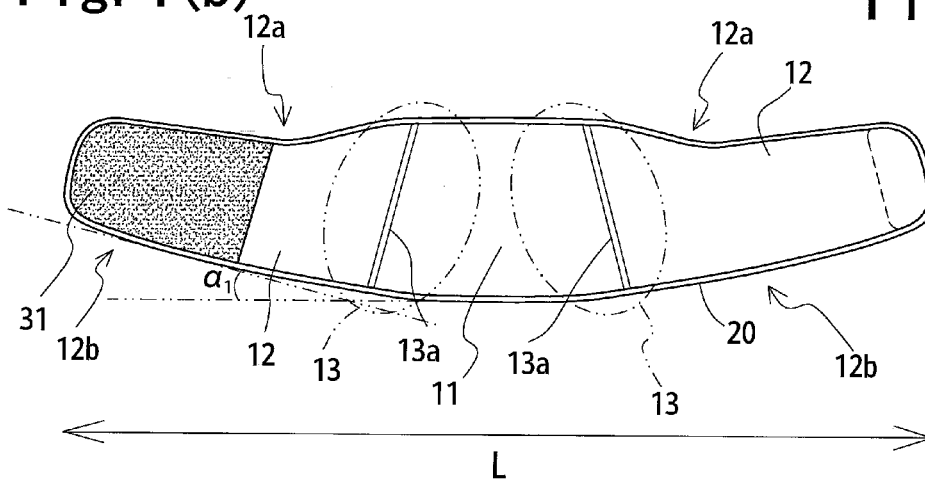
FIG. 4(b) is a diagram showing the front fabric face of the supporter shown in FIG. 4(a)
Figure 4D:
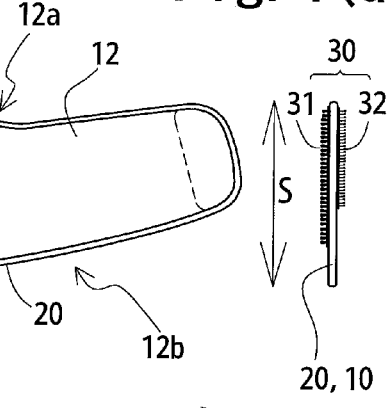
FIG. 4(d) is a left side view of the supporter shown in FIG. 4(a).
Figure 4C:
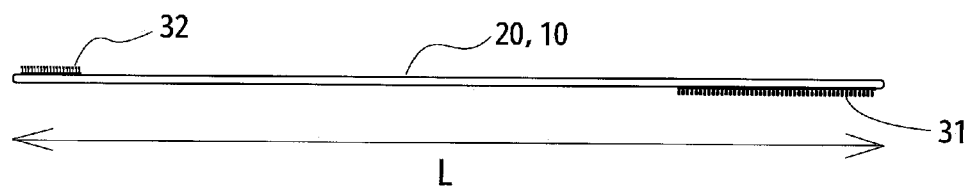
FIG. 4(c) is a lower side view of the supporter shown in FIG. 4(a)

Further, maintaining a correct posture also stabilizes the lumbar vertebrae 201, and a burden on the lumbar vertebrae 201 can be reduced by suppressing a retroflexion movement which is burdens the lumbar region most (retroflexion suppression), as shown in FIG. 3(b).

Further, oscillation of a sacrum 204 that is a foundation of the lumbar vertebrae 201 can be suppressed by tightening a sacroiliac joint 206 by applying pressure to ilia 205 from both side surface sides (stability of the sacroiliac joint).

Therefore, the supporter 100 related to this embodiment has the curved sections 13 each making the vicinity of the boundary between the back-supporting section 11 and each of the projection sections 12 be curved into a shape of approximate "/ \". In this way, in a state where the wearer wears the supporter 100, as shown in FIG. 2, the back-supporting section 11 of the base material 10 is located at a portion corresponding to the lumbar vertebrae 201 in the back of the wearer, the curved sections 13 (the upper sides 12a of both end portions) of the base material 10 are located at the lower sides (the vicinity of the ilia 205) from portions corresponding to ribs (the twelfth ribs) 207 in the lateral regions of the abdomen of the wearer, and the projection sections 12 of the base material 10 are located at the lower sides from portions corresponding to the ribs (the twelfth ribs) 207 in the preabdomen of the wearer.

That is, the projection sections 12 of the base material 10 can press the abdominal cavity 203 without being disturbed by the ribs 207 while the back-supporting section 11 of the base material 10 supports the lumbar vertebrae 201 of the wearer, whereby it is possible to give an intraperitoneal pressure rise effect to the wearer and also suppress the retroflexion of the lumbar region. Further, since the projection sections 12 of the base material 10 in the supporter 100 are located at the lower sides from the portions corresponding to the ribs (the twelfth ribs) 207 in the preabdomen of the wearer and do not press the ribs 207, forward flexion can be easily performed without inhibiting a forward flexion movement of the lumbar region (there is no hindrance in daily motion), and also, since the supporter 100 does not press the stomach of the wearer, there is no feeling of pressure on the stomach and a feeling of wearing of the supporter 100 is good.

In particular, the supporter 100 uses the base material 10 which provides stretchability in the longitudinal direction L and suppresses stretchability in the short direction S. In this way, as shown in FIGS. 2(b) and 2(d), a stretching force of the base material 10 acts in a direction of an arrow, and thus the abdomen is pushed up from below, thereby further pushing the internal organs inside the ribs 207 up, and pressure applied to the internal organs is propagated to the backbone, thereby supporting the backbone even from the inside, whereby an intraperitoneal pressure rise effect and retroflexion suppression can be further enhanced. Further, the curved sections 13 on the left and right sides of the base material 10 press the ilia 205 from the left and right side end portions 13b sides, thereby being able to tighten and stabilize the sacroiliac joint 206.

In addition, in a case where fastening by the hook-and-loop fastener 30 (the loop 31 and the hook 32) that is the fastening portion is performed, as shown in FIG. 5, a length in a circumferential direction H1 by the upper side of the base material 10 is shorter than a length in a circumferential direction H2 by the lower side of the base material 10, whereby the supporter 100 has a tapered shape (in a front view, a shape of approximate "/ \" by the left and right side end portions 13b) widening toward an end over an area from the lower sides of portions corresponding to the ribs (the twelfth ribs) 207 to a portion corresponding to the pelvis 202. For this reason, compared to a cylindrical supporter, the supporter 100 related to this embodiment is fitted to the shape of the waist of the wearer and supported by the pelvis 202, whereby position shift of the supporter 100 associated with the movement of the waist of the wearer can be prevented.

In particular, the pelvis 202 of a woman has a structure in which it is laterally wide and vertically short, compared to the pelvis 202 of a man. For this reason, in the supporter 100 for a woman, in order to surround a portion corresponding to the pelvis 202, as shown in FIG. 4, it is preferable to set the position of the uppermost end of the projection section 12 to be a position higher than the position of the upper side of the back-supporting section 11, set a length from the back-supporting section 11 to a leading end of the projection section 12 to be long compared to the supporter 100 for a man (for example, FIG. 1) having the same size, and make an angle α2 (>α1) formed by a lower side of the back-supporting section 11 and a lower side of the projection section 12 larger, thereby making a taper angle θ2 (>θ1) large.

For example, an angle α1 formed by a lower side of the back-supporting section 11 and a lower side of the projection section 12 in FIG. 1 is in a range of 14° to 18°. Then, in the supporter 100 which is formed corresponding to a range of the angle α1, if the projection sections 12 are bent with the approximately "/ \"-shaped reference lines 13a as references so as to be curved to the lower side and fastened to each other by the hook-and-loop fastener 30 that is the fastening portion, the supporter 100 in which a taper angle θ1 corresponds to a range of 5° to 7° is obtained.

Further, for example, the angle α2 formed by the lower side of the back-supporting section 11 and the lower side of the projection section 12 in FIG. 4 is in a range of 18° to 20°. Then, in the supporter 100 which is formed corresponding to a range of the angle α2, if the projection sections 12 are bent with the approximately "/ \"-shaped reference lines 13a as references so as to be curved to the lower side and fastened to each other by the hook-and-loop fastener 30 that is the fastening portion, the supporter 100 in which the taper angle θ2 corresponds to a range of 7° to 9° is obtained.

Here, a warp knitted fabric was knitted by knitting yarns impregnated with liquid for varying hardness and the supporters 100 (Example 1: a type having low hardness, and Example 2: a type having high hardness) were fabricated from a single sheet of warp knitted fabric with a knitting direction of the warp knitted fabric set to be the longitudinal direction L of the supporter 100. Then, with respect to the supporters 100 related to Examples 1 and 2, the results of measurement of an elongation rate (the percentage of a difference between a length when elongated (an elongated dimension) and the original length (the original dimension) to the original length) measured using a stretch tester (tensile load: 4.5 kg) are shown in Table below. In addition, Example 1 is related to the supporter 100 for a man by the knitting yarns impregnated with liquid having a resin concentration of 20% and Example 2 is related to the supporter 100 for a woman by the knitting yarns impregnated with liquid having a resin concentration of 25%.

TABLE 1

| Example | Measurement site | Original dimension [cm] | Elongated dimension [cm] | Elongation rate [%] |
|---|---|---|---|---|
| 1 | Longitudinal direction L between sewing lines of hook-and-loop fasteners present in both end portions (area excluding hook-and-loop fastener portion from the entire length) | 64.5 | 103.0 | 59.69 |
|   | Short direction S between upper and lower sides of back-supporting section (width (center length)) | 17.0 | 17.0 | 0.00 |
| 2 | Longitudinal direction L between sewing lines of hook-and-loop fasteners present in both end portions (area excluding hook-and-loop fastener portion from the entire length) | 75.5 | 114.0 | 50.99 |
|   | Short direction S between upper and lower sides of back-supporting section (width (center length)) | 16.0 | 16.0 | 0.00 |

According to Table 1, it is found that in the supporters 100 related to Examples 1 and 2, stretchability in the longitudinal direction L is provided and stretchability in the short direction S of the supporter 100 is suppressed (non-stretchability).

Further, in both a male subject wearing the supporter 100 related to Example 1 (elongation rate in the longitudinal direction L: 59.69%) and a female subject wearing the supporter 100 related to Example 2 (elongation rate in the longitudinal direction L: 50.99%), a feeling of wearing was good.

Next, the results verifying the operation and effects of the supporter 100 related to this embodiment will be described.

Figure 6A:
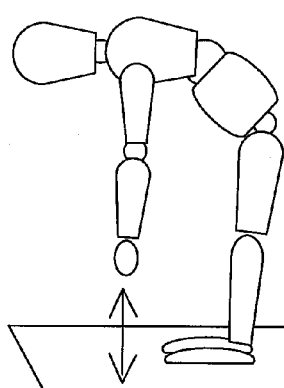
FIG. 6(a) is an explanatory diagram for explaining forward flexion that is a measured motion of a test subject.
Figure 6B:
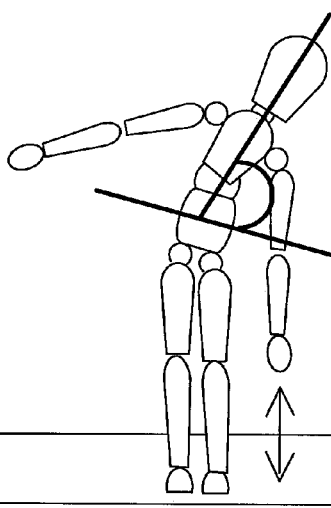
FIG. 6(b) is an explanatory diagram for explaining lateral flexion that is measurement motion of the test subject.
Figure 6C:
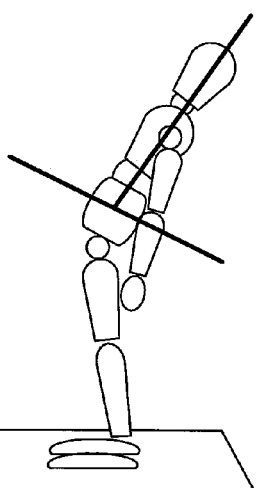
FIG. 6(c) is an explanatory diagram for explaining retroflexion that is measurement motion of the test subject.

In an experiment, in a case where the supporter 100 related to Example 1 is worn on the waist of a test subject (a 27-year-old healthy adult man, body height: 172 cm, body weight: 58 kg) (hereinafter referred to as the time of wear) and a case where the supporter 100 is not worn (hereinafter referred to as the time of non-wear), changes in the distance between a fingertip and a floor in forward flexion of the body trunk (FIG. 6(a)), the distance between the fingertip and the floor and an angle in lateral flexion (FIG. 6(b)), and an angle in retroflexion (FIG. 6(c)) were compared.

The measurement results are shown in Table 2 below and FIGS. 7 and 8.

TABLE 2

| Measurement contents | | The time of non-wear | The time of wear |
|---|---|---|---|
| Forward flexion | Distance [cm] | −9.0 | −8.5 |
| Lateral flexion | Distance [cm] | −40 | −43 |
| | Angle [°] | 49.01 | 39.67 |
| Retroflexion | Angle [°] | 46.4 | 43.9 |

Figure 7A:
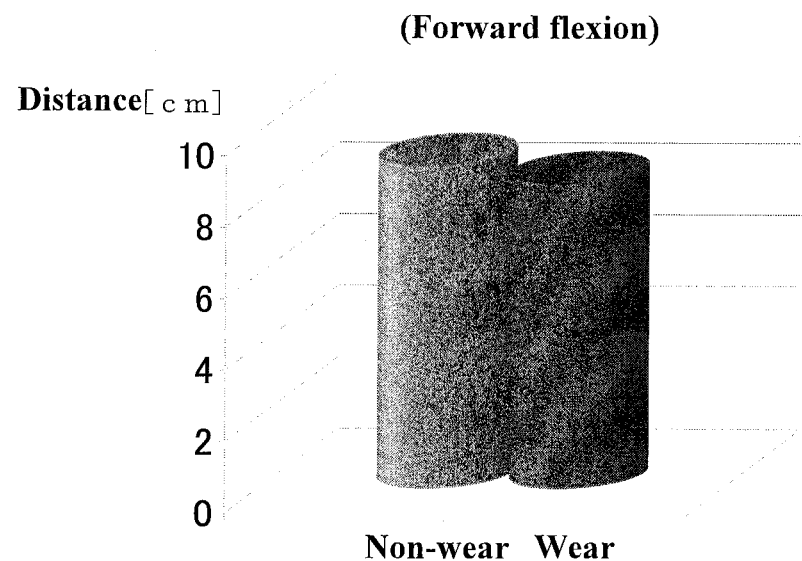
FIG. 7(a) is a graph showing the measurement results of a distance from a fingertip to a floor in forward flexion for verifying the operation and effects of the supporter.
Figure 7B:
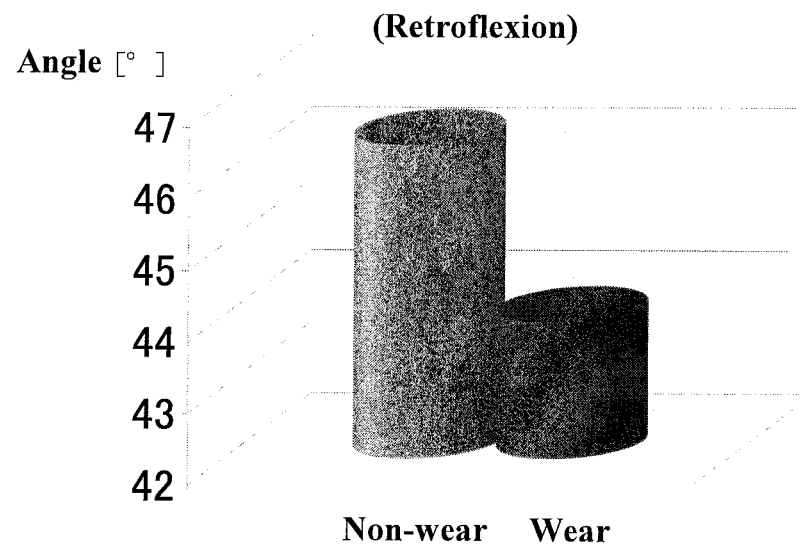
FIG. 7(b) is a graph showing the measurement results of a retroflexion angle for verifying the operation and effects of the supporter.
Figure 8A:
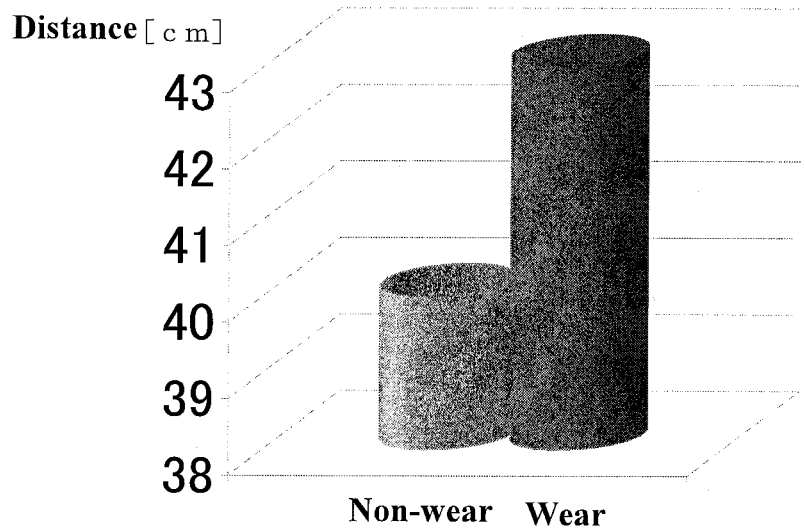
FIG. 8(a) is a graph showing the measurement results of a distance from a fingertip to a floor in lateral flexion for verifying the operation and effects of the supporter.
Figure 8B:
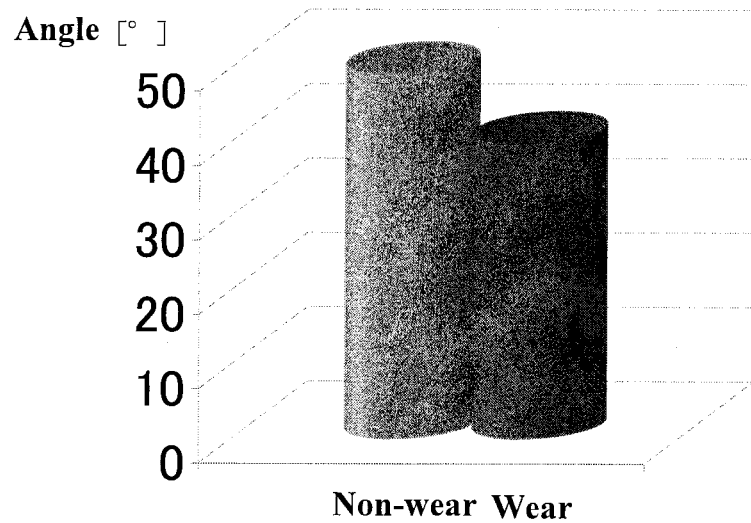
FIG. 8(b) is a graph showing the measurement results of a lateral flexion angle for verifying the operation and effects of the supporter.

As shown in Table 2 and FIGS. 7 and 8, it is found that at the time of wear of the supporter 100, compared to the time of non-wear, while there is no significant difference in distance between the fingertip and the floor in the forward flexion, the distance between the fingertip and the floor in the lateral flexion becomes long and the angles in the lateral flexion and the retroflexion become small.

That is, the supporter 100 limits ranges of the lateral flexion movement and the retroflexion movement in the wearer without limiting a range of the forward flexion movement in the wearer (the same degree as that at the time of non-wear) and exhibits the operation and effects in which it is possible to suppress retroflexion movement which burdens the lumbar region most.

Second Embodiment of the Invention

FIG. 9(a) is a diagram showing the back fabric face of a supporter related to a second embodiment, FIG. 9(b) is a diagram showing the front fabric face of the supporter shown in FIG. 9(a), FIG. 9(c) is a lower side view of the supporter shown in FIG. 9(a), and FIG. 9(d) is a left side view of the supporter shown in FIG. 9(a). In FIG. 9, the same reference numeral as that in FIG. 1 denotes the same or equivalent section and description thereof is omitted.

The projection section 12 has a pressing section 40 which is disposed at an area to press the abdominal cavity 203 of the wearer in a case where fastening by the hook-and-loop fastener 30 (the loop 31 and the hook 32) that is the fastening portion is performed and which suppresses the stretchability in the longitudinal direction L of the base material 10. The pressing section 40 is formed, for example, by coating, attaching, or spray-depositing resin onto the base material 10.

In addition, the pressing section 40 related to this embodiment is disposed continuously onto the hook 32 on the same surface of the base material 10 such that the shape of the entirety of the pressing section 40 and the hook 32 in the drawing showing the back fabric face of FIG. 9(a) appears approximately symmetrically to the overall shape of the loop 31 in the drawing showing the front fabric face of FIG. 9(b).

Further, since the hook-and-loop fastener 30 (the loop 31 and the hook 32) is a member having no stretchability, the hook-and-loop fastener 30 suppresses the stretchability in the longitudinal direction L of the base material 10 along with the pressing section 40.

In particular, since the hook 32 of the hook-and-loop fastener 30 is a member having no stretchability, by disposing the hook 32 even in an area where the pressing section 40 should be disposed, the pressing section 40 need not be disposed (the hook 32 may also share the pressing section 40).

In addition, the second embodiment is different from the first embodiment only in that the pressing section 40 is newly disposed at the projection section 12, and except the operation and effects by the pressing section 40, which are described below, the same operation and effects as those in the first embodiment are exhibited.

The pressing section 40 exhibits the operation and effects in which the pressing section 40 suppresses the stretchability in the longitudinal direction L of the base material 10, thereby preventing pressure which is applied to the abdominal cavity 203 of the wearer from being distributed in the longitudinal direction L of the base material 10 due to extension of the base material 10, and thus it is possible to intensively apply pressure to the abdominal cavity 203 and it is possible to enhance the intraperitoneal pressure rise effect described above.

Third Embodiment of the Invention

Figure 10A:
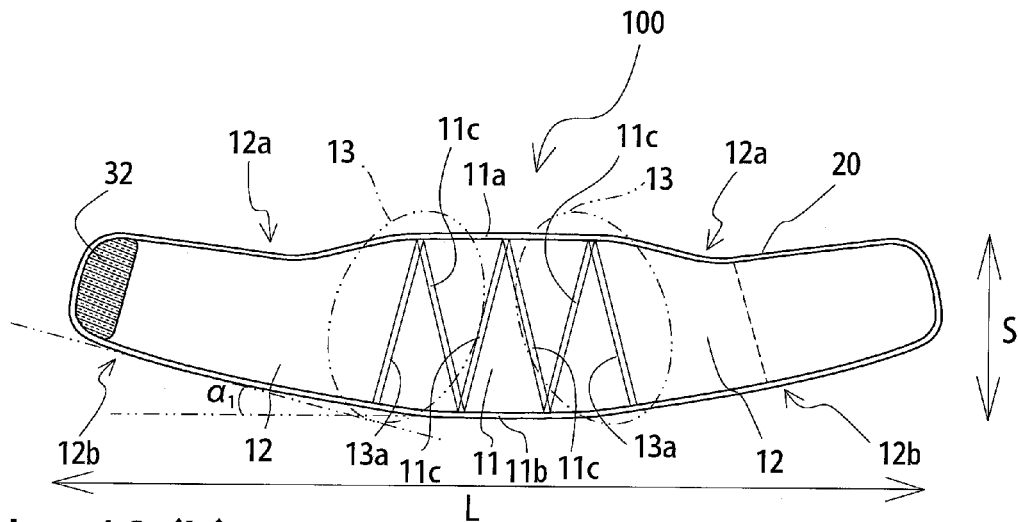
FIG. 10(a) is a diagram showing the back fabric face of a supporter related to a third embodiment.
Figure 10B:
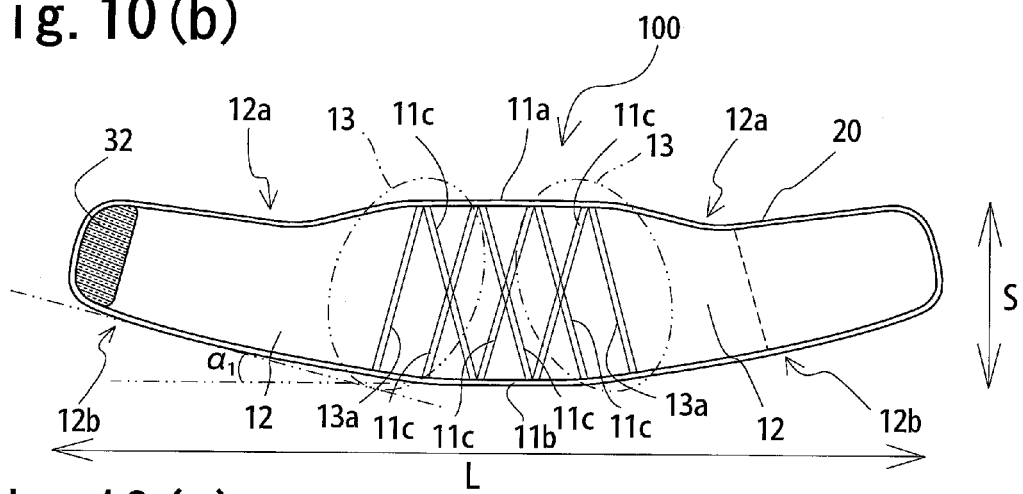
FIG. 10(b) is a diagram showing the back fabric face of another supporter related to the third embodiment.

FIG. 10(a) is a diagram showing the back fabric face of a supporter related to a third embodiment, and FIG. 10(b) is a diagram showing the back fabric face of another supporter related to the third embodiment. In FIGS. 10(a) and 10(b), the same reference numeral as that in FIG. 1(a) denotes the same or equivalent section and description thereof is omitted.

The back-supporting section 11 has a supporting portion 11c that is formed by a stitch, pad sewing, or adhesive interlining which traverses between an upper side 11a and a lower side 11b, and that suppresses bending of the back-supporting section 11 in the short direction S of the base material 10.

In addition, the supporting portion 11c, that is formed by a stitch, is formed by a stitch by, for example, a two-needle or three-needle sewing machine with respect to the base material 10.

Further, the supporting portion 11c that is formed by pad sewing is formed by applying and sewing a cloth (a patch) or the like which is separately applied for the purpose of reinforcement, with respect to the base material 10.

Further, the supporting portion 11c that is formed by adhesive interlining is formed by applying adhesive resin made of, for example, resin of a type such as polyester-based resin, polyamide-based resin, polyurethane-based resin, polyethylene-based (high density or low density) resin, or ethylene vinyl acetate-based resin to the base material 10 by a processing method such as dot processing, powder processing, cobweb processing, or film processing, and carrying out heating and pressurizing treatment with a flat type press machine, a roller type press machine, or the like, thereby fixing the resin to the fabric.

In addition, the third embodiment is different from the first embodiment only in that the supporting portion 11c is newly disposed at the back-supporting section 11, and except the operation and effects by the supporting portion 11c, which are described below, the same operation and effects as those in the first embodiment are exhibited.

In the supporter 100 related to this embodiment, the operation and effects are exhibited in where the back-supporting section 11 has the supporting portion 11c, whereby it is possible to suppress bending of the back-supporting section 11 in the short direction S of the base material 10 while maintaining the curved surface of the back-supporting section 11 along the curvature of the lumbar region of the wearer, thereby preventing curling of the back-supporting section 11, and bring the supporter 100 into close contact with the lumbar region of the wearer.

In particular, as shown in FIG. 10(a) or 10(b), the supporting portion 11c diagonally traverses between the upper side 11a and the lower side 11b of the back-supporting section 11, whereby it is possible to suppress the stretchability in the longitudinal direction L of the base material 10. Accordingly, the back-supporting section 11 functions as an anchor with respect to the base material 10 in which stretchability is provided in the longitudinal direction L between the back-supporting section 11 and a portion of the projection section 12 in which the hook-and-loop fastener 30 is disposed, along with the projection section 12 in which the stretchability in the longitudinal direction L of the base material 10 is suppressed due to the hook-and-loop fastener 30.

In addition, as long as it suppresses the bending of the back-supporting section 11 in the short direction S of the base material 10, the supporting portion 11c related to this embodiment is not limited to the number, the position, the size, and the range as shown in FIGS. 10(a) and 10(b), and it is preferable to appropriately set the number, the position, the size, and the range in accordance with the material, the shape, and the size of the base material 10 (the back-supporting section 11).

Fourth Embodiment of the Invention

Figure 10C:
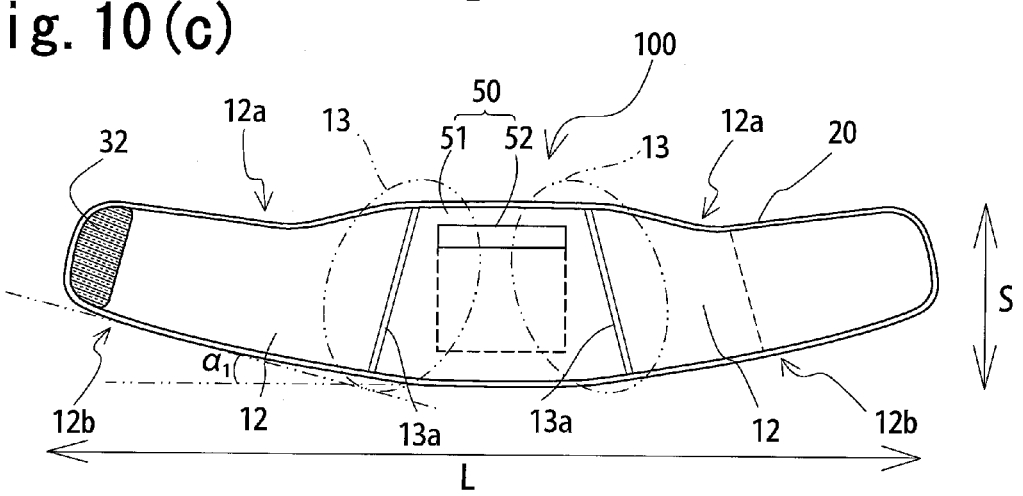
FIG. 10(c) is a diagram showing the back fabric face of a supporter related to a fourth embodiment.
Figure 11:
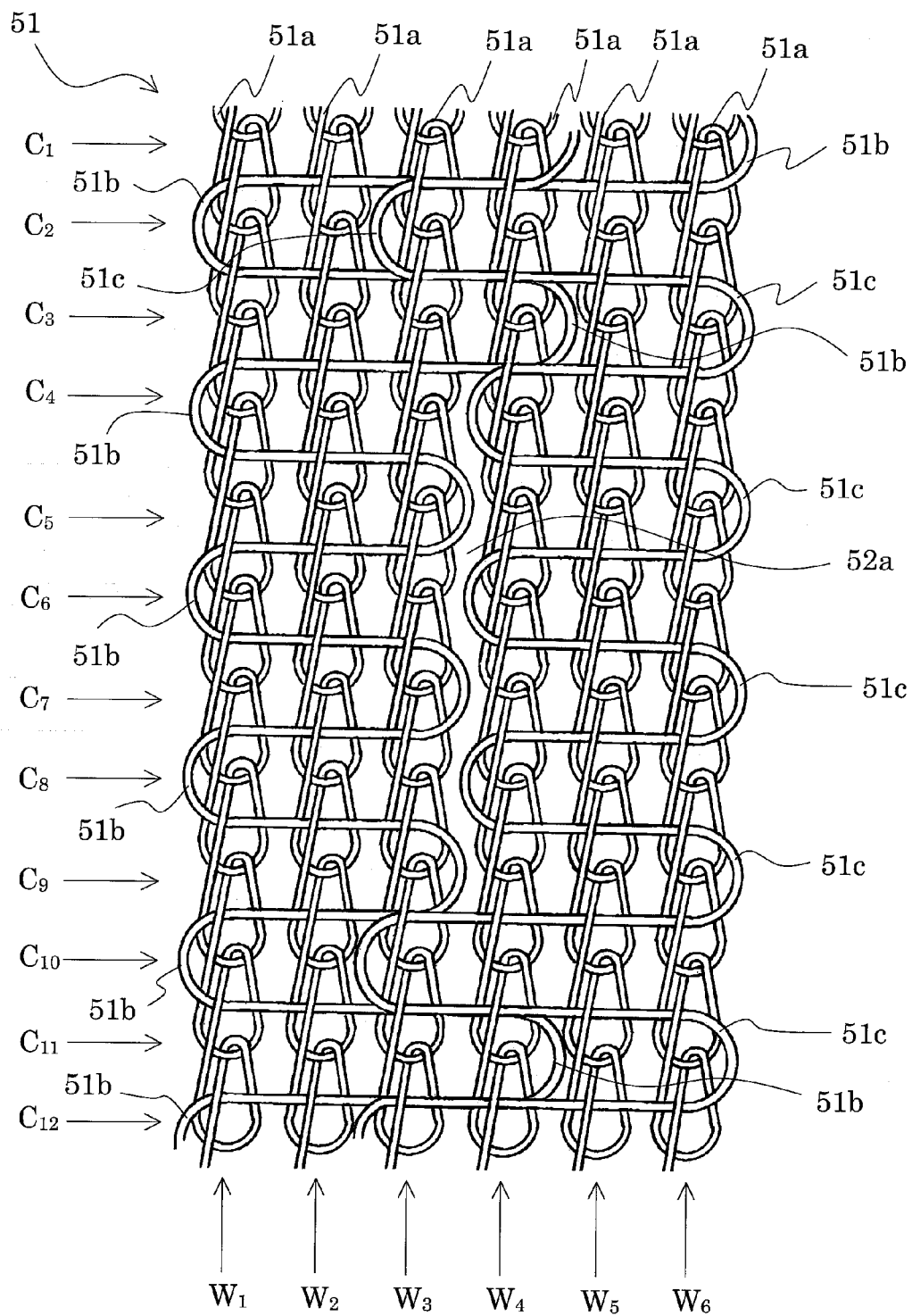
FIG. 11 is a schematic configuration diagram of a knitting weave forming a back-support facing section of the supporter related to the fourth embodiment.

FIG. 10(c) is a diagram showing the back fabric face of a supporter related to a fourth embodiment. FIG. 11 is a schematic configuration diagram of a knitting weave forming a back-support facing section of the supporter related to the fourth embodiment. In FIG. 10(c), the same reference numeral as that in FIG. 1(a) denotes the same or equivalent section and description thereof is omitted.

A receiving section 50 is a pouch-like container sewn to the back-supporting section 11 of the base material 10 and is for putting, for example, a stay such as a plastic or metal piece for reinforcing the back-supporting section 11 or an accessory such as a portable body warmer therein. In FIG. 10(c), the receiving section 50 is disposed on the back fabric face. However, the receiving section 50 may also be disposed on the front fabric face. Further, in the case of a use to put a portable body warmer in the receiving section 50, the receiving section 50 may also be disposed at the projection section 12 other than the back-supporting section 11, and the receiving section 50 may also be disposed at plurality places.

In addition, the receiving section 50 related to this embodiment is for receiving a portable body warmer (not shown) therein and is formed by forming an insertion opening 52 for the portable body warmer by cutting a portion of a cloth or a knitted fabric (hereinafter referred to as a back-support facing section 51) having a shape corresponding to the back-supporting section 11 of the base material 10 and sewing a cut edge, and applying the back-support facing section 51 to the back-supporting section 11 of the base material 10 and then sewing the circumference so as to double as the reference lines 13a, as shown in FIG. 10(c). In particular, an upper side and a lower side of the back-support facing section 51 may also be sewn inserted in the binder tape 20 along with the edge (the cut face) of the base material 10.

Further, in a case of forming the back-support facing section 51 by using a warp knitted fabric, a crochet warp knitting machine is used as a knitting machine knitting the back-support facing section 51 and a slit 52a is formed in the warp knitted fabric which is knitted by warp knitting yarns 51a constituting wales W and weft insertion yarns traveling in directions of courses C, and the slit 52a may also be used as the insertion opening 52.

For example, as shown in FIG. 11, in a case of forming the slit 52a between a third wale $W_3$ and a fourth wale $W_4$ and in a fourth course $C_4$ to a ninth course $C_9$, knitting is performed as follows.

In the warp knitted fabric shown in FIG. 11, in order to connect chain stitches of three wales (a first wale $W_1$, a second wale $W_2$, and the third wale $W_3$) in the fourth course $C_4$ to the ninth course $C_9$, turn-back end portions of a first weft insertion yarn 51b are formed at the first wale $W_1$ and the third wale $W_3$, and in order to connect chain stitches of three wales (the fourth wale $W_4$, a fifth wale $W_9$, and a sixth wale $W_6$) in the fourth course $C_4$ to the ninth course $C_9$, turn-back end portions of a second weft insertion yarn 51c are formed at the fourth wale $W_4$ and the sixth wale $W_6$.

Then, in the warp knitted fabric shown in FIG. 11, the first weft insertion yarn 51b and the second weft insertion yarn 51c overlap one another between a first course $C_1$ and a second course $C_2$, between the second course $C_2$ and a third course $C_3$, between the ninth course $C_9$ and a tenth course $C_{10}$, and between the tenth course $C_{10}$ and an eleventh course $C_{11}$ in the third wale $W_3$ and the fourth wale $W_4$.

In this manner, by forming the back-support facing section 51 by using a warp knitted fabric, and forming the slit 52a in the warp knitted fabric so as to provide the insertion opening 52, a processing of performing cutting for forming a cut edge that becomes the insertion opening 52 and a process of sewing the cut edge can be omitted, and thus the number of production processes and the production cost of the insertion opening 52 can be reduced.

In addition, the fourth embodiment is different from the first embodiment only in that the receiving section 50 is newly disposed at the back-supporting section 11, and except the operation and effects by the receiving section 50, which are described below, the same operation and effects as those in the first embodiment are exhibited.

The receiving section 50 related to this embodiment can accommodate accessories according to the needs of the wearer, thereby increasing convenience of the supporter 100, and in particular, in a case of receiving a stay therein, the operation and effects are exhibited in which it can make it possible to perform adjustment of the hardness of the back-supporting section 11.

Other Embodiments

In the first embodiment described above, by using the base material 10 in which a knitting direction of a warp knitted fabric is set to be the longitudinal direction L of the supporter 100, stretchability in the longitudinal direction L is provided without using warp yarns having stretchability. However, warp yarns having stretchability may also be used.

Further, the supporter 100 related to the first embodiment described above has been described with regard to a case of using it as a supporter for the waist. However, the supporter 100 can also be used as a supporter such as a supporter for the abdomen, a supporter for the pelvis, or a supporter for the ilia.

REFERENCE SIGNS LIST

10: base material
11: back-supporting section
11a: upper side
11b: lower side
11c: supporting portion
12: projection section
12a: upper side
12b: lower side
13: curved section
13a: reference line
13b: side end portion
20: binder tape
30: hook-and-loop fastener
31: loop
32: hook
40: pressing section
50: receiving section
51: back-support facing section 51*a*: warp knitting yarn
51*b*: first weft insertion yarn
51*c*: second weft insertion yarn
52: insertion opening
52*a*: slit
100: supporter
201: lumbar vertebrae
202: pelvis
203: abdominal cavity
204: sacrum
205: ilium
206: sacroiliac joint
207: rib
L: longitudinal direction
S: short direction

The invention claimed is:

1. A supporter including a base material constructed from a single sheet of knitted fabric continuously knitted by warp knitting and in which a knitting direction of the single sheet of knitted fabric is set to be a longitudinal direction, and stretchability in the longitudinal direction is given, while stretchability in a short direction is suppressed, the supporter comprising:
 a back-supporting section that is a central portion of the base material;
 projection sections provided by projecting upward both end portions of the base material which are respectively disposed on both sides of the back-supporting section; and
 fastening portions which are disposed on different surfaces of the projection sections and which are adapted to fasten the different surfaces to each other,
 wherein an upper side of each of the projection sections forms a curved concave portion and a lower side of each of the projection sections forms an approximate arc shape which is continuous along with a lower side of the back-supporting section, and
 in a case where the different surfaces of the projection sections are fastened to each other by the fastening portions, a length in a circumferential direction by an upper side of the base material is shorter than a length in a circumferential direction by a lower side of the base material, therefore the vicinity of the boundary between the back-supporting section and each of the projection sections curve into an approximate tapered shape.

2. The supporter according to claim 1, wherein the different surfaces of the projection sections are configured to be fastened to each other by the fastening portions with a lower side of the base material being continuous.

3. The supporter according to claim 1, further comprising:
 a pressing section which is adapted to be disposed at an area to press an abdominal cavity of a wearer in a case where the different surfaces of the projection sections are fastened to each other by the fastening portions and which is adapted to suppress stretchability in the longitudinal direction of the base material.

4. The supporter according to claim 1, wherein the back-supporting section has a supporting portion that is constructed by a stitch, pad sewing, or adhesive interlining which traverses between an upper side and a lower side, and that is adapted to suppress bending of the back-supporting section in the short direction of the base material.

5. The supporter according to claim 1, wherein the approximate tapered shape is configured to narrow from a pelvis area of a wearer to a rib area of the wearer.

\* \* \* \* \*